(12) United States Patent
Besson

(10) Patent No.: US 6,324,241 B1
(45) Date of Patent: Nov. 27, 2001

(54) METHOD AND APPARATUS FOR CT RECONSTRUCTION

(75) Inventor: Guy M. Besson, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/475,386

(22) Filed: Dec. 30, 1999

(51) Int. Cl.$^7$ ........................................ A61B 6/03
(52) U.S. Cl. .................. 378/4; 378/19; 378/901
(58) Field of Search .................. 378/4, 15, 19, 378/901

(56) References Cited

U.S. PATENT DOCUMENTS

| | | | |
|---|---|---|---|
| 4,549,265 | * 10/1985 | Deckers et al. | 378/14 |
| 4,852,132 | 7/1989 | Namikawa | 378/19 |
| 5,999,587 | * 12/1999 | Ning et al. | 379/4 |
| 6,075,836 | * 6/2000 | Ning | 378/98.12 |
| 6,173,032 | 1/2001 | Besson . | |
| 6,233,308 | * 5/2001 | Hsieh | 378/62 |
| 6,246,742 | * 6/2001 | Besson et al. | 378/8 |

OTHER PUBLICATIONS

U.S. application No. 09/162,284, G. Besson, filed Sep. 29, 1998 (copy not attached).
G. Besson, "CT fan–beam parameterizations leading to shift–invariant filtering," Inverse Probl. 12, pp. 815–833, 1996.
Berthold K.P. Horn, "Fan–Beam Reconstruction Methods," Proceedings of the IEEE, vol. 67, No. 12, pp. 1616–1623, Dec. 1979.
Berthold, K.P. Horn, "Density Reconstruction Using Arbitrary Ray–Sampling Schemes," Proceedings of the IEEE, vol. 66, No. 5, pp. 551–562, May 1978.

* cited by examiner

*Primary Examiner*—David V. Bruce
(74) *Attorney, Agent, or Firm*—Armstrong Teasdale, LLP; Christian G. Cabou

(57) ABSTRACT

In one embodiment, the present invention is a method for reconstructing a scanned CT image that includes steps of: acquiring projection data of an object utilizing a flat-panel detector; and filtering and backprojecting the projection data, without radially interpolating, to reconstruct a three-dimensional image of the object. This embodiment provides direct fan-parallel, three-dimensional reconstruction of computed tomographic images without loss of resolution associated with radial interpolation, while retaining imaging quality and backprojection speed gains associated with parallel reconstruction.

16 Claims, 5 Drawing Sheets

METHOD AND APPARATUS FOR CT RECONSTRUCTION

BACKGROUND OF THE INVENTION

This invention relates to methods and apparatus for volumetric computed tomograph (CT) reconstruction and more specifically to methods and apparatus for fan parallel cone beam volumetric CT reconstruction utilizing a flat panel detector.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Three-dimensional reconstruction of scanned CT images is possible. A direct fan parallel reconstruction method is used for data acquired using a flat panel detector. The use of parallel reconstruction advantageously provides an amount of aliasing cancellation. However, in at least one known method, a radial interpolation step is required when rebinning from fan beam to parallel data. This interpolation step produces a loss of resolution.

It would therefore be desirable to provide methods and apparatus for direct fan parallel, three dimensional reconstruction of computed tomographic images that avoid the loss of resolution associated with radial interpolation and that retain the image quality and backprojection speed gains associated with parallel reconstruction.

BRIEF SUMMARY OF THE INVENTION

There is therefore provided, in one embodiment, a method for reconstructing a scanned CT image that includes steps of: acquiring projection data of an object utilizing a flat-panel detector; and filtering and backprojecting the projection data, without radially interpolating, to reconstruct a three-dimensional image of the object.

The above described embodiment provides direct fan-parallel, three-dimensional reconstruction of computed tomographic images without loss of resolution associated with radial interpolation, while retaining imaging quality and backprojection speed gains associated with parallel reconstruction.

DETAILED DESCRIPTION OF THE INVENTION

Figure 1:
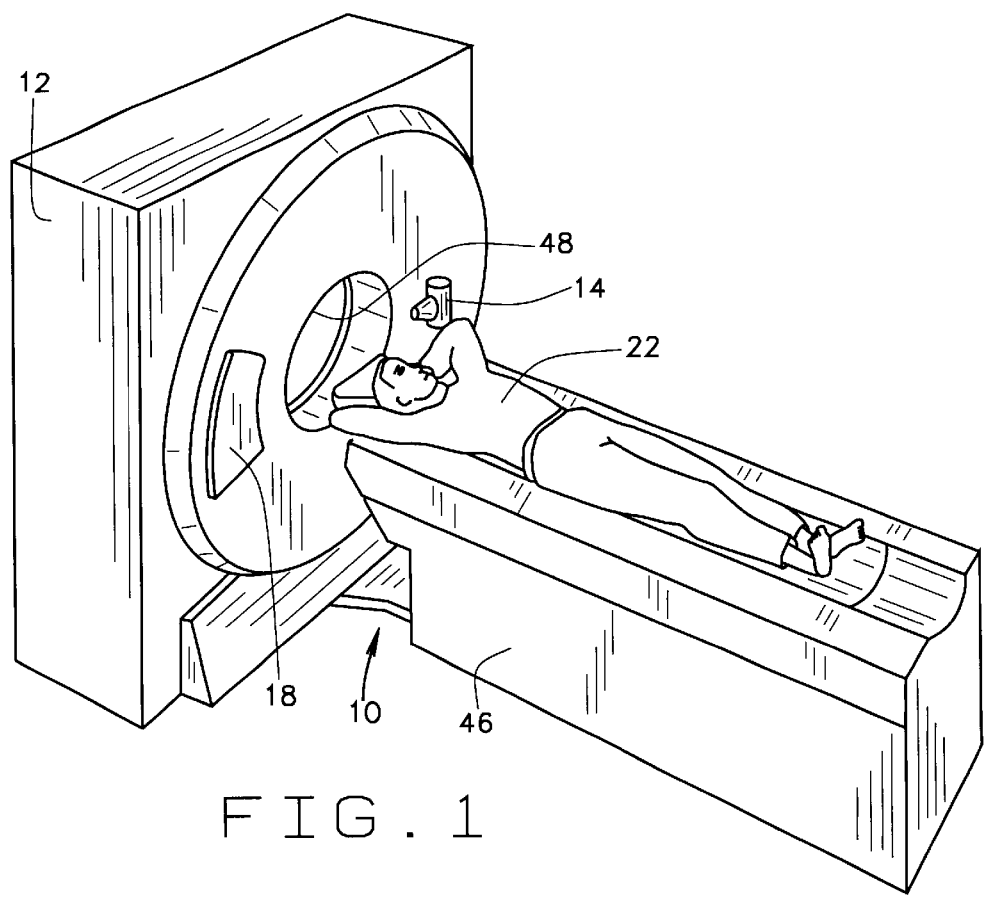
FIG. 1 is a pictorial view of a CT imaging system.
Figure 2:
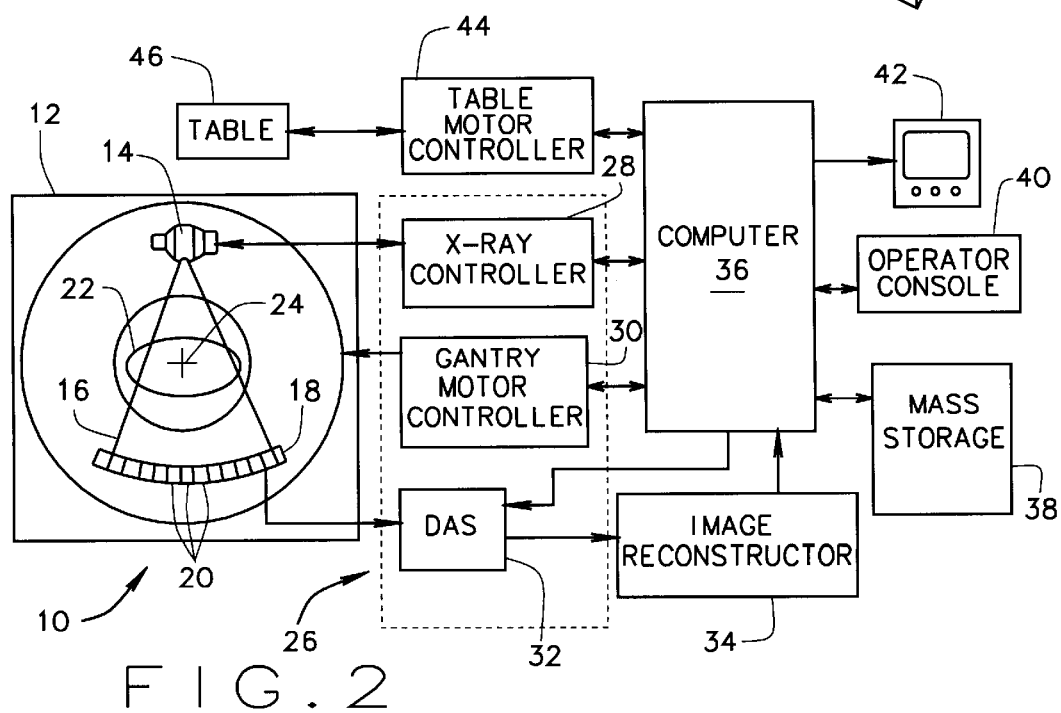
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements or cells 20 which together sense the projected x-rays that pass through an object 22, for example a medical patient. Detector array 18 may be fabricated in a single slice or multi-slice configuration, and also, in various shapes, such as an arc of a circle, an arc of a cylinder, or flat panels. Each detector element or cell 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment of the present invention, a fan-parallel weighted-convolution reconstruction kernel decomposition is utilized. Let $f(r,\phi)$ and $\underline{f}(x,y)$ denote respectively polar and cartesian representations of an x-ray attenuation coefficient distribution to be reconstructed, and $p(s,\theta)$ a polar representation of a Radon transform of $\underline{f}$:

$$p(s, \theta) = \int_{-\infty}^{\infty}\int_{-\infty}^{\infty} \underline{f}(x, y)\delta(x\cos\theta + y\sin\theta - s)dxdy \quad (1)$$

Figure 3:
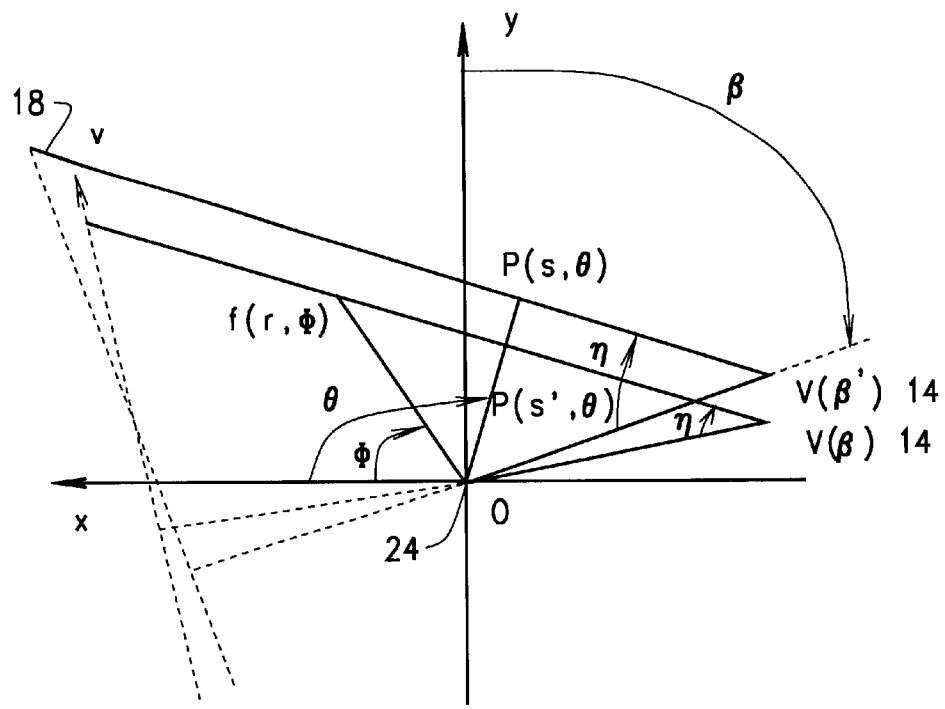
FIG. 3 is a representation of fan beam and fan parallel geometries for one fan formed by a row of a planar two-dimensional detector orthogonal to the system z-axis and a fan-vertex V.

Under conditions satisfied by any patient or scanned object, and referring to FIG. 3, the Radon inversion formula is written as:

$$f(r, \phi) = \frac{1}{4\pi^2}\int_0^{2\pi}\lim_{\varepsilon \to 0}\int_{-\infty}^{\infty} F_\varepsilon(t)p(s, \theta)dsd\theta \quad (2)$$

with:

$$t = s - r\cos(\theta - \phi) \quad (3)$$

and:

$$F_\varepsilon(t) = \begin{pmatrix} \frac{1}{\varepsilon^2} & |t| \le \varepsilon \\ \frac{-1}{t^2} & |t| \ge \varepsilon \end{pmatrix} \quad (4)$$

where FIG. 3 illustrates fan-beam and fan-parallel geometries for one fan formed by a horizontal row of a planar two-dimensional detector and fan vertex V. Two source positions (from vertices) are shown at two angles, β and β'.

Figure 4:
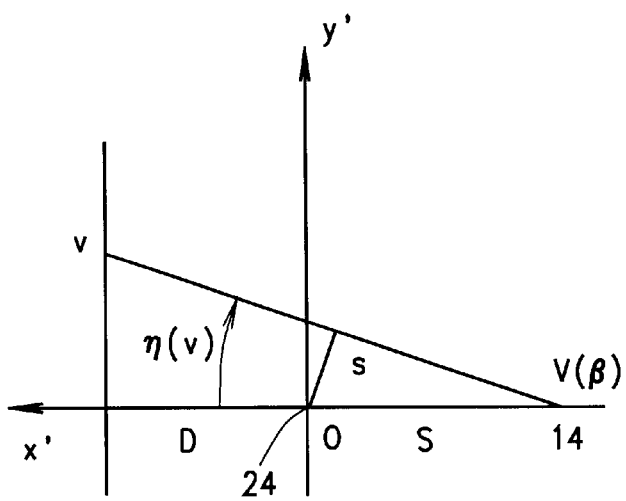
FIG. 4 is a representation of geometry for a fan-beam projection defined by readings of a row of detector cells.

In the following, the Radon space parameterization $(s,\theta)$ is changed into the fan-beam parameterization $(\beta, \eta(v))$, and the integral is then expressed as a weighted convolution. Reference is made to FIG. 3 discussed above, and to FIG. 4, which is a representation of geometry for one fan beam projection defined by the readings of a row of detector cells in plane x'Oy'. S and D are, respectively, distances from fan-vertex V and the detector plane to O; E=S+D, and s is a Radon distance (in the plane of FIG. 4) associated with a ray detected at detector cell position υ. Introducing β, an angle from the y axis to fan-vertex V, S, a distance from vertex V to O and P, a point to be reconstructed, projection data $p(s,\theta)$ is parameterized via angle η from VO to VP (see FIG. 3), with η(0)=0 and η limited to $[\eta_{min},\eta_{max}]$ so that an entire object cross-section (bounded in an image plane) is covered. Parameters (β,v) are independent variables, with β being a source (vertex) angle and v a detector cell coordinate on a straight line defined by an intersection of an imaging plane and detector 18 plane. Changing variables $(s,\theta) \to (\beta,v)$ via the parameterization η(v) produces:

$$\begin{bmatrix} \theta \\ S \end{bmatrix} = \begin{bmatrix} \beta + \eta(v) \\ S \sin[\eta(v)] \end{bmatrix}. \quad (5)$$

Parameter limits are defined by $\beta_{min}, \beta_{max}, v_{min}, v_{max}$ so that:

$$\beta_{max} - \beta_{min} = 2\pi; \ \eta(v_{min}) = \eta_{min}; \ \eta(v_{max}) = \eta_{max}. \quad (6)$$

For a flat-panel detector 18, and considering all data to be filtered to be acquired along a single "horizontal" detector row, fan-beam parameterization is given by:

$$\eta(v) = \arctan\left[\frac{v}{S+D}\right] = \arctan\left[\frac{v}{E}\right], \quad (7)$$

where E=S+D is a sum of distances from source V to isocenter O, and D from O to detector 18 (as measured along a ray from V to detector 18 through O).

The Jacobian of the transformation is written as:

$$J = \frac{S \times E \times \cos\left[\arctan\left(\frac{v}{E}\right)\right]}{E^2 + v^2} = \frac{S}{E}\frac{1}{\left(\left[1 + \left(\frac{v}{E}\right)^2\right]\right)^{3/2}}. \quad (8)$$

Variable t, the argument of F is written as:

$$t = s - r\cos(\theta - \phi)$$

so that:

$$t = S \times \sin[\eta(v)] - r\cos(\theta - \phi). \quad (9)$$

In fan-parallel reconstruction, as in parallel reconstruction, angle θ is constant for one fan-parallel projection, unlike the case in fan-beam reconstruction. Defining a fan-angle for a ray passing through point $f(r,\phi)$ to be reconstructed:

$$\eta = \eta(v) \text{ with: } S \times \sin[\eta] = r\cos(\theta - \phi), \quad (10)$$

argument t is written as:

$$t = S \times \{\sin[\eta(v)] - \sin[\eta(\tilde{v})]\} = \left\{\frac{\sin[\eta(v)] - \sin[\eta(\tilde{v})]}{v - \tilde{v}}\right\} \times S \times (v - \tilde{v}) \quad (11)$$

The following relation is used below:

$$\lim_{\varepsilon \to 0}\int_{-\infty}^{\infty} F_\varepsilon[\lambda b(\lambda)]a(\lambda)d\lambda = \lim_{\varepsilon \to 0}\int_{-\infty}^{\infty} F_\varepsilon(\lambda)\frac{a(\lambda)}{b^2(\lambda)}d\lambda. \quad (12)$$

Considering F, with t as above (11), then, under the summation sign:

$$F_\varepsilon(t) = F_\varepsilon(v - \tilde{v}) \times \frac{1}{S^2} \times \left\{\frac{v - \tilde{v}}{\sin[\eta(v)] - \sin[\eta(\tilde{v})]}\right\}^2. \quad (13)$$

Let K be written as:

$$K(v, \tilde{v}) = \left\{ \frac{\sin[\eta(v)] - \sin[\eta(\tilde{v})]}{v - \tilde{v}} \right\} \quad (14)$$

If K can be written as a weighted convolution kernel:

$$K(v, \tilde{v}) = \left\{ \frac{\sin[\eta(v)] - \sin[\eta(\tilde{v})]}{v - \tilde{v}} \right\} = E(v)H(v - \tilde{v})G(\tilde{v}) \quad (15)$$

where H is a convolution kernel, and E and G are pre- and post-convolution weights (E(v) as used here is not to be confused with the constant E introduced in equation (7)), then:

$$F_\varepsilon(t) = \frac{F_\varepsilon(v - \tilde{v})}{S^2 \times [E(v)H(v - \tilde{v})G(\tilde{v})]^2} \quad (16)$$

is also in the form of a weighted-convolution (shift-invariant filtering). Note that Jacobian J (equation (8)) is a function of η, and therefore contributes a pre-convolution weight only. The reconstruction equation is thus written in the form of a weighted-convolution backprojection:

$$f(r, \phi) = \quad (17)$$

$$\frac{1}{4\pi^2 S^2} \int_0^{2\pi} \frac{1}{G(\tilde{v})^2} \left\{ \lim_{\varepsilon \to 0} \int_{v_{inf}}^{v_{sup}} \frac{f_\varepsilon(v - \tilde{v})}{H^2(v - \tilde{v})} \times \frac{J(v)}{E(v)^2} \times p(\beta, v) dv \right\} d\beta$$

In equation (17), the $$\frac{J(v)}{E(v)^2}$$

term corresponds to a pre-filtering weighting; the bracketed {} expression corresponds to a filtering operation; the term $$\frac{1}{G(\tilde{v})^2}$$

corresponds to a post-filtering weighting; the integral over dβ corresponds to a backprojection operation; and the term $$\frac{1}{4\pi^2 S^2}$$

corresponds to a normalization factor. Also:
 r, φ, and θ are polar coordinates in a polar coordinate system;
 f(r,φ) is a polar representation of an x-ray attenuation coefficient distribution to be reconstructed;
 v is a detector cell coordinate on a straight line defined by an intersection of an imaging plane and a plane defined by the flat panel detector;
 β is an angle from a y-axis to a radiation source;
 p(β,v) is a representation of a radon transform of f, which itself is a Cartesian representation of an x-ray attenuation distribution to be reconstructed;
 S is a distance from a radiation source to an isocenter;
 $v_{sup}$ is a maximum detector cell coordinate on flat panel 18;

$v_{inf}$ is a minimum detector cell coordinate;
 H(v−v) and $F_\varepsilon$(v−v) are convolution kernels;
 η(v) is a fan angle for a ray passing through a voxel being reconstructed, and v is a cell index for the ray;
 E(v) is a preconvolution weight that is a function of detector cell position v;
 G(v) is a post convolution weighting; and
 J(v) is a Jacobian function.

Standard techniques for adapting integrals to algorithms operating on discrete data are known and need not be described in detail here. In embodiments of the present invention, such techniques are used to approximate integrals such as those in equation (17). Thus, filtering and backprojection comprises a discrete reconstruction of an image as an approximation to the continuous weighted-convolution backprojection of equation (17).

In one embodiment of the invention, after acquiring projection data of an object utilizing a flat panel detector, image reconstruction proceeds as follows, according to equation (17), looping over projections corresponding to parameter β for each fixed image point. For a given projection, apply a pre-convolution weighting to the projection data using function E and Jacobian J; noting that pre-convolution weights are independent of an image point described by (r,φ)). Next, perform a convolution using kernels F and H, and apply a post-convolution weighting using function G; independent of the image point. Finally, perform a backprojection, and, in one embodiment, apply a normalization factor. Note that a pixel-dependent weighted fan-beam backprojection is not required for fan-parallel backprojection.

Necessary condition for reconstruction

A necessary condition for the fan-parallel kernel K to be decomposed as:

$$K(v, \tilde{v}) = \left\{ \frac{\sin[\eta(v)] - \sin[\eta(\tilde{v})]}{v - \tilde{v}} \right\} = E(v)H(v - \tilde{v})G(\tilde{v}) \quad (18)$$

can be expressed in term of the fan-beam parameterization η as:

$$K(v, \tilde{v}) = \left\{ \frac{\sin[\eta(v)] - \sin[\eta(\tilde{v})]}{v - \tilde{v}} \right\} = \quad (19)$$

$$\left\{ \frac{\eta'(v)\cos[\eta(v)]\eta'(\tilde{v})\cos[\eta(\tilde{v})]}{\eta'(0)\eta'(v - \tilde{v})\cos[\eta(v - \tilde{v})]} \right\}^{1/2} \frac{\sin[\eta(v - \tilde{v})]}{v - \tilde{v}}.$$

Equivalently, the following necessary condition is written for η:

$$\sin[\eta(v)] - \sin[\eta(\tilde{v})] = \left\{ \frac{\eta'(v)\cos[\eta(v)]\eta'(\tilde{v})\cos[\eta(\tilde{v})]}{\eta'(0)\eta'(v - \tilde{v})\cos[\eta(v - \tilde{v})]} \right\}^{1/2} \sin[\eta(v - \tilde{v})]. \quad (20)$$

In equation (20), η(v) is a fan angle as a function of detector cell 20 coordinate v.

From (4) and (5) it is written that:

$$v = E \times \tan[\arcsin(\alpha)], \quad (21)$$

where α is a coordinate describing equidistant increments, is a solution. As is shown below, an equidistant parameterization written as:

$$\eta(v) = \arctan\left[\frac{v}{S+D}\right] = \arctan\left[\frac{v}{E}\right], \quad (22)$$

associated with flat-panels with equidistant detector cells, is not a solution to equation (20). Yet an approximate solution provided by the necessary condition (and henceforth referred to as a "natural approximation") is a very close one that leads to excellent imaging results.

Fan-parallel CT reconstruction from flat-panel detector

Substituting the parameterization (22) into the necessary condition (20) leads to an approximate relation written as:

$$K(v, \tilde{v}) = \left\{\frac{\sin[\eta(v)] - \sin[\eta(v)]}{v - \tilde{v}}\right\} = \frac{\sqrt{1+\left(\frac{v}{E}\right)^2} - \sqrt{1+\left(\frac{\tilde{v}}{E}\right)^2}}{v - \tilde{v}}, \quad (23)$$

$$K(v, \tilde{v}) \approx \left\{\frac{E^2[E^2 + (v-\tilde{v})^2]}{(E^2 + v^2)(E^2 + \tilde{v}^2)} \times \frac{\cosarctan\left(\frac{v}{E}\right)\cosarctan\left(\frac{\tilde{v}}{E}\right)}{\cosarctan\left(\frac{v-\tilde{v}}{E}\right)}\right\}^{1/2} \quad (24)$$

$$\frac{\sinarctan\left(\frac{v-\tilde{v}}{E}\right)}{v-\tilde{v}}$$

which, using trigonometric relations, is rewritten as:

$$K(v, \tilde{v}) = \quad (25)$$

$$\frac{\frac{v}{\sqrt{1+\left(\frac{v}{E}\right)^2}} - \frac{\tilde{v}}{\sqrt{1+\left(\frac{\tilde{v}}{E}\right)^2}}}{v-\tilde{v}} \approx \frac{1}{E} \frac{\left[1+\left(\frac{v-\tilde{v}}{E}\right)^2\right]^{1/4}}{\left[1+\left(\frac{v}{E}\right)^2\right]^{3/4}\left[1+\left(\frac{\tilde{v}}{E}\right)^2\right]^{3/4}}$$

Accordingly, by substitution into (17), to the following image reconstruction algorithm $$f(r, \phi) \approx \frac{1}{4\pi^2} \frac{E}{S} \quad (26)$$

$$\int_0^{2\pi} \lim_{\varepsilon \to 0} \int_{v_{min}}^{v_{max}} \left[1+\left(\frac{\tilde{v}}{E}\right)^2\right]^{3/2} \times \frac{F_\varepsilon(v-\tilde{v})}{\sqrt{1+\left(\frac{v-\tilde{v}}{E}\right)^2}} \times p(\beta, v) dv d\beta$$

Recalling equation (4) for the Jacobian, an expression for pre-convolution weights is identically constant and equal to 1.0, and a filter expression is written as:

$$\frac{F_\varepsilon(v-\tilde{v})}{\left[1+\left(\frac{v-\tilde{v}}{E}\right)^2\right]^{1/2}} = F_\varepsilon(v-\tilde{v})\cos[\eta(v-\tilde{v})]. \quad (27)$$

Post-convolution weights are written:

$$\left[1+\left(\frac{\tilde{v}}{E}\right)^2\right]^{3/2} = \frac{1}{\cos^3(\tilde{\eta})} \quad (28)$$

For comparison purposes, a 2D fan-beam reconstruction formula for straight-line of detector cells is:

$$f(r, \phi) =$$

$$\frac{1}{4\pi^2} \int_0^{2\pi} \lim_{\varepsilon \to 0} \int_{v_{min}}^{v_{max}} \left(\frac{S}{L}\right)^2 \frac{1}{\cos^2(\tilde{\eta})} \times F_\varepsilon(v-\tilde{v}) \times p(\beta, v)\cos[\eta(v)] dv d\beta$$

The pre- and post-convolution weight expressions and filter expression of this embodiment differ from those for Feldkamp reconstruction (as well as fan-beam reconstruction from a straight line of detectors) and are unique to direct fan-parallel image reconstruction from a straight line of detector. For example, the $1/L^2$ of fan-beam reconstruction is absent from the equation for fan-parallel reconstruction.

Cone-beam fan-parallel reconstruction for a circular source trajectory

Figure 5:
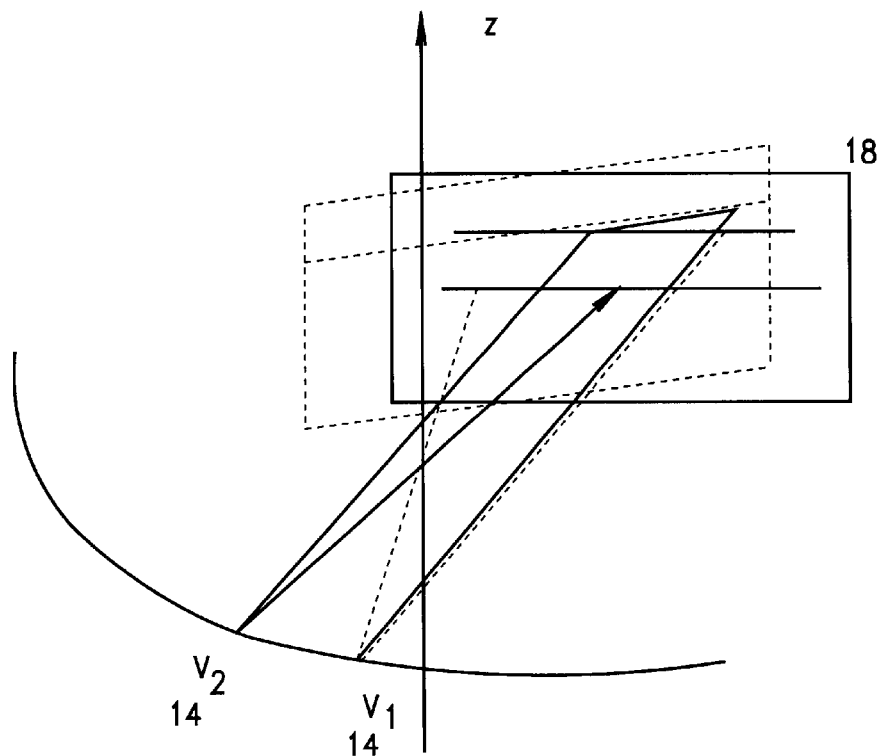
FIG. 5 is a geometric representation of a rebinning process of one embodiment of the present invention in which rebinning is to a fan-parallel geometry for a flat panel detector and a circular source trajectory.
Figure 6:
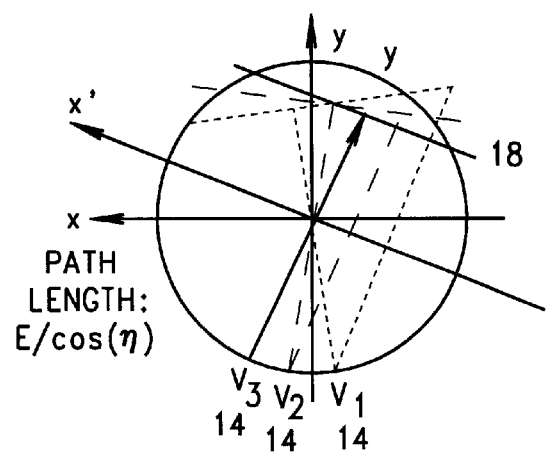
FIG. 6 is a different representation of the geometry of the rebinning process illustrated in FIG. 5.
Figure 8:
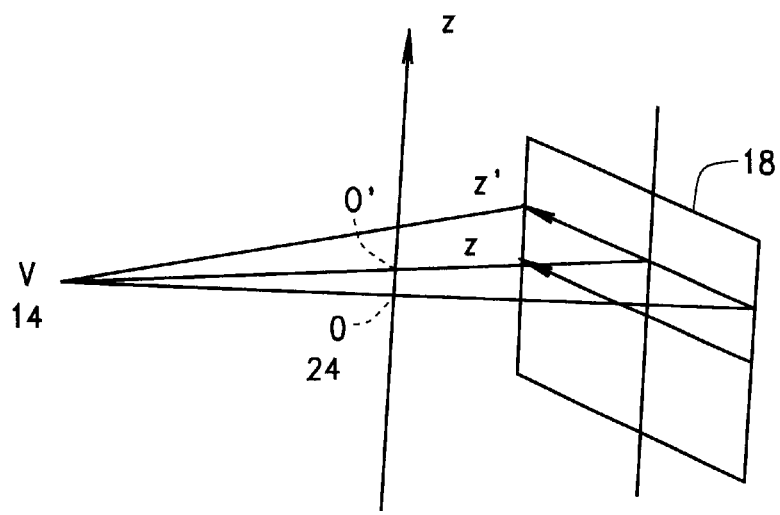
FIG. 8 is a drawing that shows a representation of an orthogonal projection of a scanner isocenter onto a plane defined by an xy line of detector cells and a cone vertex defined by an x-ray source and that defines a tilted plane defined by the vertex and a an axis x' parallel to and offset from an x axis.

In one embodiment, rebining is done on a row-by-row basis, to define an associated fan-parallel geometry. In addition, the $d\beta$ infinitesimal is changed to $d\beta'$ to account for a fan average cone-angle and fan geometry is adapted to account for tilting of the fan beam away from a central gantry plane, i.e., an equivalent source rotation in a tilted plane. See FIGS. 5 and 6, which are graphical illustration of the process of rebinning to a fan-parallel geometry for a flat panel detector and a circular source trajectory. See also FIG. 8, in which O' is an orthogonal projection of a scanner 10 isocenter onto a plane defined by an xy line of detector cells 20 and cone vertex V represents x-ray source 14. A tilted fan is defined by V and an axis x' parallel to and offset from z. O is on a central (or gantry 12) plane. The central plane is orthogonal to z and passes through V.

Cone-beam fan-parallel reconstruction for a helical source trajectory

Figure 7:
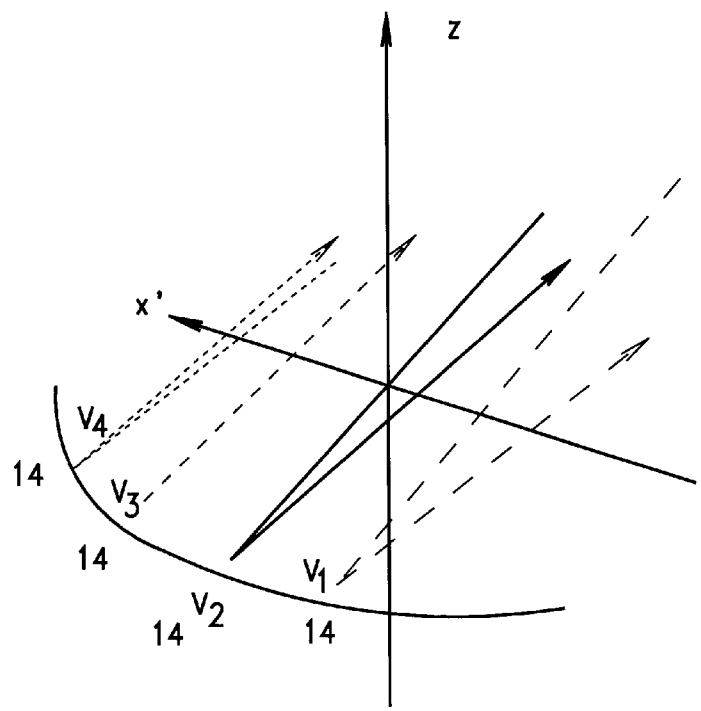
FIG. 7 is a geometric representation of a rebinning process of one embodiment of the present invention, where rebinning is to a fan parallel geometry for a flat parallel detector and a helical source trajectory.

In one embodiment employing a helical source trajectory, and referring to FIG. 7, rays are rebinned to fan-parallel by interpolating a projection along z, so that the rays intersect an associated fan-parallel x'=t axis at a constant elevation. A weight is included to account for individual ray cone-angles, and an average cone-angle of the fan-parallel projection (equal to the cone-angle for the ray at $\gamma=0$) is used to calculate $d\beta'$ in the tilted plane. Backprojection then proceeds on a voxel basis, as in the FDK algorithm.

Figure 9:
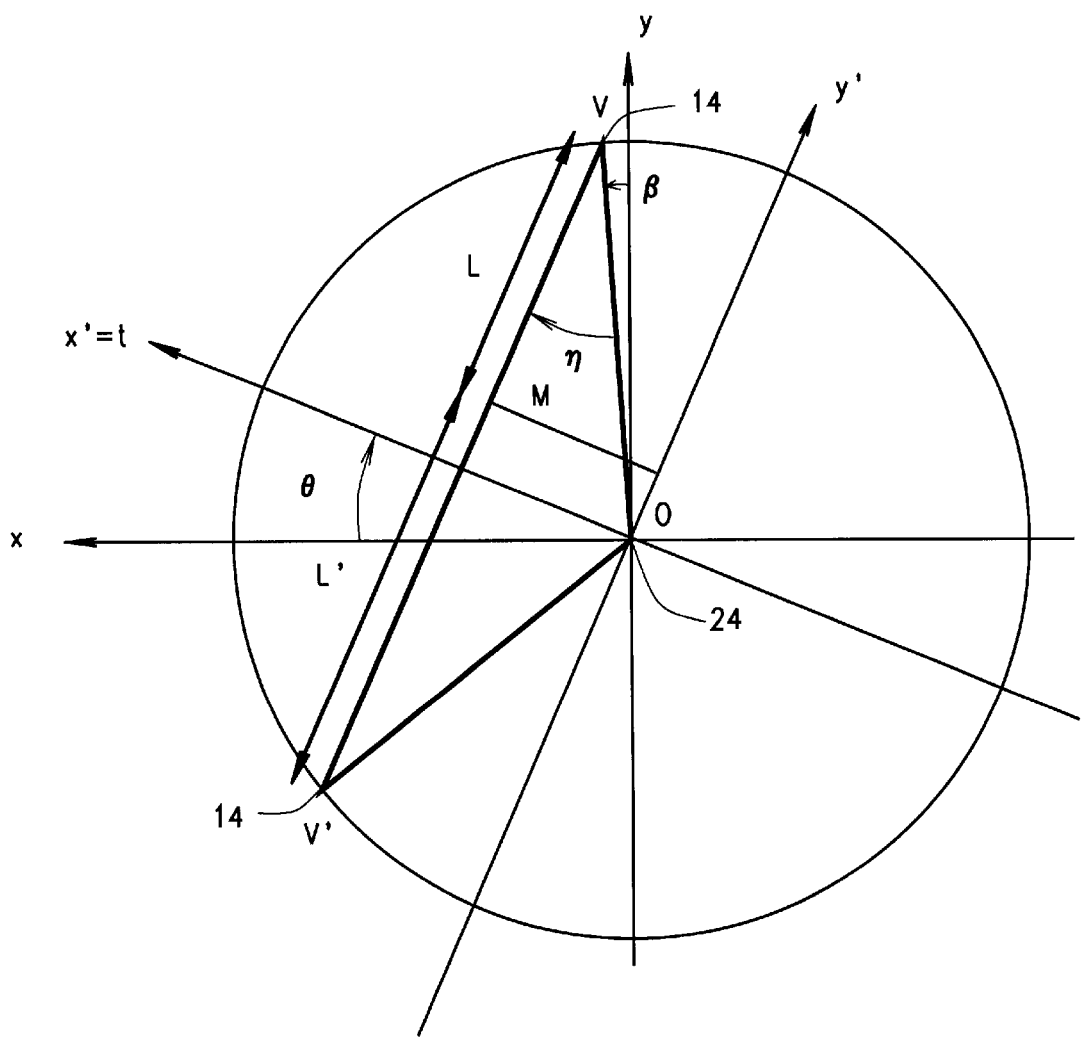
FIG. 9 is a geometric representation of a voxel M to be reconstructed.

From the preceding description of various embodiments of the present invention, it is evident that fan-parallel, three-dimensional reconstruction of computed tomographic images is achieved without loss of resolution associated with radial interpolation and without the loss of aliasing cancellation due to the $1/L^2$ factor in fan-beam reconstruction. Referring to FIG. 9, in fan beam reconstruction, the two conjugate rays contributing to M (from source 14 positions V and V') have unequal weights (except on x'); therefore limiting aliasing cancellation effectiveness away from isocenter 24 (as $L \neq L', 1/L^2 \neq 1/L'^2$). This same consideration explains why noise in reconstructed images increases away from isocenter 24 in fan-beam reconstruction (assuming a constant noise level in backprojection data). Both of these effects (aliasing cancellation and noise) are improved with fan-parallel backprojection, due to the absence of the $1/L^2$ factor in reconstruction equation (26).

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

What is claimed is:

1. A method for reconstructing a scanned CT image comprising the steps of:
   acquiring projection data of an object utilizing a flat-panel detector having a plurality of detector cells; and
   filtering and backprojecting the projection data, without radially interpolating, to reconstruct a three-dimensional image of the object.

2. A method in accordance with claim 1, wherein filtering and backprojecting the projection data comprises the step of discretely reconstructing the image as an approximation to a continuous weighted-convolution backprojection written as:

$$f(r, \phi) = \frac{1}{4\pi^2 S^2} \int_0^{2\pi} \frac{1}{G(\tilde{v})^2} \left\{ \lim_{\varepsilon \to 0} \int_{v_{inf}}^{v_{sup}} \frac{f_\varepsilon(v - \tilde{v})}{H^2(v - \tilde{v})} \times \frac{J(v)}{E(v)} \times p(\beta, v) dv \right\} d\beta$$

where:
   r, $\phi$, and $\theta$ are polar coordinates in a polar coordinate system;
   $f(r,\phi)$ is a polar representation of an x-ray attenuation coefficient distribution to be reconstructed;
   v is a detector cell coordinate on a straight line defined by an intersection of an imaging plane and a plane defined by the flat panel detector;
   $\beta$ is an angle from a y-axis to a radiation source;
   $p(\beta,v)$ is a representation of a radon transform of $\underline{f}$, which itself is a Cartesian representation of an x-ray attenuation distribution to be reconstructed;
   S is a distance from a radiation source to an isocenter;
   $v_{sup}$ is a maximum detector cell coordinate on the flat panel detector;
   $v_{inf}$ is a minimum detector cell coordinate;
   $H(v-v)$ and $F_\varepsilon(v-v)$ are convolution kernels;
   $\eta(v)$ is a fan angle for a ray passing through a voxel being reconstructed, and v is a cell index for the ray;
   $E(v)$ is a preconvolution weight that is a function of detector cell position v;
   $G(v)$ is a post convolution weighting; and
   $J(v)$ is a Jacobian function.

3. A method in accordance with claim 2 wherein the pre-convolution weights are independent of an image point described by $(r,\phi)$.

4. A method in accordance with claim 2, wherein:

$$\sin[\eta(v)] - \sin[\eta(\tilde{v})] = \left\{ \frac{\eta'(v)\cos[\eta(v)]\eta'(\tilde{v})\cos[\eta(\tilde{v})]}{\eta'(0)\eta'(v-v')\cos[\eta(v-\tilde{v})]} \right\}^{1/2} \sin[\eta(v-\tilde{v})];$$

where $\eta(v)$ is a fan angle as a function of detector cell coordinate v.

5. A method in accordance with claim 2, wherein acquiring projection data of an object utilizing a flat-panel detector comprises the step of acquiring projection data of the object utilizing a cone beam of radiation from a radiation source having a circular trajectory.

6. A method in accordance with claim 5 wherein the detector is a multi-row detector and further comprising the step of rebinning data on a row-by-row basis.

7. A method in accordance with claim 2 wherein acquiring projection data of an object utilizing a flat-panel detector comprises the step of acquiring projection data of the object utilizing a cone beam of radiation from a radiation source having a helical trajectory.

8. A method in accordance with claim 7 wherein the detector is a multi-row detector and further comprising the steps of weighting the projection data to account for individual ray cone-angles, and using an average cone angle of a fan-parallel projection equal to a cone angle for a ray at $\eta=0$ to determine $d\beta'$ in a tilted plane, where $d\beta'$ is a source rotation in the tilted plane.

9. A CT imaging system having a flat panel radiation detector and a radiation source, the flat panel radiation detector having a plurality of detector cells, and said imaging system being configured to:
   acquire projection data of an object utilizing the flat-panel detector; and
   filter and backproject the projection data, without radially interpolating, to reconstruct a three-dimensional image of the object.

10. A CT imaging system in accordance with claim 9, wherein said system being configured to filter and backproject the projection data comprises said system being configured to reconstruct the image as a weighted-convolution backprojection written as:

$$f(r, \phi) = \frac{1}{4\pi^2 S^2} \int_0^{2\pi} \frac{1}{G(\tilde{v})^2} \left\{ \lim_{\varepsilon \to 0} \int_{v_{inf}}^{v_{sup}} \frac{f_\varepsilon(v - \tilde{v})}{H^2(v - \tilde{v})} \times \frac{J(v)}{E(v)} \times p(\beta, v) dv \right\} d\beta$$

where:
   r, $\phi$, and $\theta$ are polar coordinates in a polar coordinate system;
   $f(r,\phi)$ is a polar representation of an x-ray attenuation coefficient distribution to be reconstructed;
   v is a detector cell coordinate on a straight line defined by an intersection of an imaging plane and a plane defined by the flat panel detector;
   $\beta$ is an angle from a y-axis to a radiation source;
   $p(\beta,v)$ is a representation of a radon transform of $\underline{f}$, which itself is a Cartesian representation of an x-ray attenuation distribution to be reconstructed;
   S is a distance from a radiation source to an isocenter;
   $v_{sup}$ is a maximum detector cell coordinate on the flat panel detector;
   $v_{inf}$ is a minimum detector cell coordinate;
   $H(v-v)$ and $F_\varepsilon(v-v)$ are convolution kernels;
   $\eta(v)$ is a fan angle for a ray passing through a voxel being reconstructed, and v is a cell index for the ray;
   $E(v)$ is a preconvolution weight that is a function of detector cell position v;
   $G(v)$ is a post convolution weighting; and
   $J(v)$ is a Jacobian function.

11. A CT imaging system in accordance with claim 10 wherein the pre-convolution weights are independent of an image point described by $(r,\phi)$.

12. A CT imaging system in accordance with claim 10, wherein:

$$\sin[\eta(\nu)] - \sin[\eta(\tilde{\nu})] = \left\{ \frac{\eta'(\nu)\cos[\eta(\nu)]\eta'(\tilde{\nu})\cos[\eta(\tilde{\nu})]}{\eta'(0)\eta'(\nu-\nu')\cos[\eta(\nu-\tilde{\nu})]} \right\}^{1/2} \sin[\eta(\nu-\tilde{\nu})];$$

where η is a fan angle associated with a detector cell indexed by ν.

13. A CT imaging system in accordance with claim 10, wherein said system being configured to acquire projection data of an object utilizing a flat-panel detector comprises said system being configured to acquire projection data of the object utilizing a cone beam of radiation from the radiation source in a circular trajectory.

14. A CT imaging system in accordance with claim 13 wherein the radiation detector is a multi-row detector, the CT imaging system further being configured to rebin data on a row-by-row basis.

15. A CT imaging system in accordance with claim 10 wherein said imaging system being configured to acquire projection data of an object utilizing a flat-panel detector comprises said system being configured to acquire projection data of the object utilizing a cone beam of radiation from the radiation source in a helical trajectory.

16. A CT imaging system in accordance with claim 15 wherein the radiation detector is a multi-row detector and said imaging system is further configured to weight the projection data to account for individual ray cone-angles, and and use an average cone angle of a fan-parallel projection equal to a cone angle for a ray at η=0 to determine dβ' in a tilted plane, where dβ' is a source rotation in the tilted plane.

* * * * *

UNITED STATES PATENT AND TRADEMARK OFFICE
CERTIFICATE OF CORRECTION

PATENT NO. : 6,324,241 B1
DATED : November 27, 2001
INVENTOR(S) : Besson

It is certified that error appears in the above-identified patent and that said Letters Patent is hereby corrected as shown below:

Column 9
Line 20, delete "$E(v)$" insert -- $E(v)^2$ --.
Line 41, delete "$H(v - v)$ and $F_\in(v - v)$" and insert therefor
-- $H(v - \widetilde{v})$ and $F_\in(v - \widetilde{v})$ --

Line 42, delete "$\eta(v)$" and insert therefor -- $\eta(\widetilde{v})$ --
Line 43, delete "$v$" and insert therefor -- $\widetilde{v}$ --

Line 46, delete "$G(v)$" and insert therefor -- $G(\widetilde{v})$ --

Line 55, delete "$(v - v)$" and insert therefor -- $(v - \widetilde{v})$ --

Column 10,
Line 32, delete "$E(v)$" insert -- $E(v)^2$ --.
Line 54, delete "$H(v - v)$ and $F_\in(v - v)$" and insert therefor
-- $H(v - \widetilde{v})$ and $F_\in(v - \widetilde{v})$ --

Line 55, delete "$\eta(v)$" and insert therefor -- $\eta(\widetilde{v})$ --
Line 56, delete "$v$" and insert therefor -- $\widetilde{v}$ --

Line 59, delete "$G(v)$" and insert therefor -- $G(\widetilde{v})$ --

Column 11,
Line 3, delete "$(v - v)$" and insert therefor -- $(v - \widetilde{v})$ --

UNITED STATES PATENT AND TRADEMARK OFFICE
CERTIFICATE OF CORRECTION

PATENT NO.    : 6,324,241 B1
DATED         : November 27, 2001
INVENTOR(S)   : Besson It is certified that error appears in the above-identified patent and that said Letters Patent is hereby corrected as shown below:

<u>Column 12,</u>
Line 12, delete "and and" and insert therefore -- and --.

Signed and Sealed this

Thirtieth Day of September, 2003

JAMES E. ROGAN
*Director of the United States Patent and Trademark Office*